United States Patent [19]

Kocak

[11] Patent Number: 4,705,511
[45] Date of Patent: Nov. 10, 1987

[54] INTRODUCER SHEATH ASSEMBLY

[75] Inventor: Nuri Kocak, Cliffside Park, N.J.

[73] Assignee: Bipore, Inc., Demarest, N.J.

[21] Appl. No.: 860,645

[22] Filed: May 7, 1986

Related U.S. Application Data

[63] Continuation-in-part of Ser. No. 6,733,556, May 13, 1985, Pat. No. 4,634,432.

[51] Int. Cl.$^4$ ...................... A61M 25/00; A61M 5/00
[52] U.S. Cl. .................................... 604/282; 604/167
[58] Field of Search ............... 604/167, 169, 280, 288, 604/264, 256; 128/657, 658, 398.1; 137/845–849; 138/174

[56] References Cited

U.S. PATENT DOCUMENTS

| | | | |
|---|---|---|---|
| 3,426,744 | 2/1969 | Ball | 604/282 |
| 4,000,739 | 1/1977 | Stevens | 604/280 |
| 4,100,309 | 7/1978 | Micklus et al. | 427/2 |
| 4,240,411 | 12/1980 | Hosono | 604/167 |
| 4,261,357 | 4/1981 | Kontos | 604/167 |
| 4,424,833 | 1/1984 | Spector et al. | 604/167 |

Primary Examiner—Stephen C. Pellegrino
Attorney, Agent, or Firm—Popper, Bobis & Jackson

[57] ABSTRACT

An introducer sheath includes a connector body having an inlet and an outlet; a flexible tube for intravenous use at the outlet, including a helical coiled spring having a plurality of coils, each coil spaced from an adjacent coil, and a thin cylindrical wall prepared from a protective coating composition completely surrounding the spring to define an inner and an outer wall surface, the cylindrical wall surrounding said spring having a substantially constant wall thickness throughout its length, the coating composition comprising a thermoplastic polymeric material dissolved in a solvent solution, the composition having a solids content ranging from about 4% to about 18%, and said solution comprising a solvent selected from the group consisting of tetrahydrofuran, dioxane, methyl ethyl ketone, dimethylformamide, cyclohexane, and mixtures thereof, formed on a helical coiled spring by dipping the latter therein and then drying at room temperature; and a valve assembly including a first elastic membrane having a central aperture, and a second elastic membrane in sealing contact with the first elastic membrane and having a slit extending therethrough at an angle to the direction of fluid flow in the introducer sheath, the slit being in fluid communication with the central aperture.

28 Claims, 7 Drawing Figures

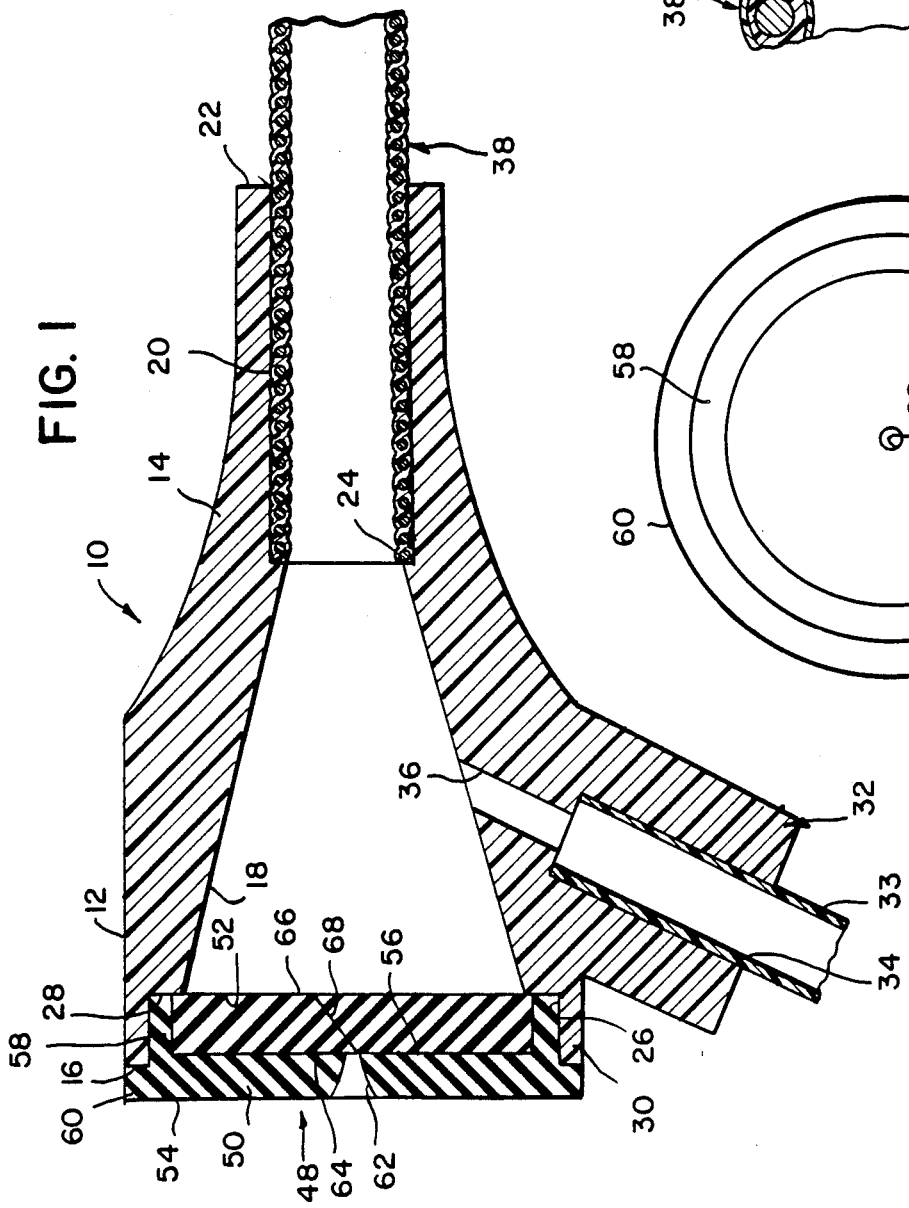

INTRODUCER SHEATH ASSEMBLY

REFERENCE TO RELATED APPLICATION

This application is a continuation-in-part of U.S. patent application Ser. No. 733,556, filed May 13, 1985, entitled Introducer Sheath Assembly, to the same Applicant herein, now U.S. Pat. No. 4,634,432.

BACKGROUND OF THE INVENTION

The present invention relates generally to introducer sheaths and, more particularly, to a novel intravenous tube and valve assembly for use therewith.

It is well known to medically treat a patient by intravenously introducing fluids into an artery or vein. In this regard, an introducer sheath or hemostasis cannula assembly is generally provided, for example, similar to that disclosed in U.S. Pat. No. 4,000,739. As shown and described in this patent, the main body portion of the assembly has a tapered portion at the outlet side thereof within which is positioned a length of flexible tubing. The catheter is inserted into the assembly through the gasket assembly at the inlet side of the main body, whereby the gasket assembly provides a fluid-tight seal. After the catheter is in position, fluid may be injected through the catheter into the vascular system for treatment of the patient.

A problem with conventional flexible tubes used with introducer sheath assemblies is that the tube walls tend to collapse or kink when flexed, such as may occur when the patient moves, and flow reduction or stoppage may result. Recent developments have attempted to overcome this problem by utilizing a helical coiled spring as part of the flexible tube, for example, as shown in U.S. Pat. Nos. 3,618,613; 3,841,308; 3,963,856; 4,044,765; 4,052,989; 4,068,660; and 4,368,730. For related, but less relevant subject matter, see also U.S. Pat. Nos. 2,437,542; 2,472,483; 4,362,163; and 4,425,919. Generally, however, the formation of such inert plastic tubing with the helical coiled spring requires either that the plastic be heat shrunk or heat bonded to the spring or force fit with respect thereto. The problem with using a force fit or extrusion coating method is that, if the wire of the spring has an extremely small diameter, which is generally necessary, it cannot withstand the forces applied during such methods. In addition, the use of heat to cure the plastic material could not be used with a plastic spring since the coil itself would melt. Accordingly, it is generally necessary to provide relatively large gauge coils, thereby reducing the density of the coils and the kink resistance properties.

U.S. Pat. No. 4,044,765 discloses an outer tubular sheath formed of a heat-shrinkable material, while an inner coating or lining is deposited by a solution, emulsion or dispersion of the same type of inert plastic as that used for the outer sheath and which is dried or cured by heating the entire unit to about 250° F. for about 10 minutes. The outer sheath, however, is still necessary in this patent for the purpose of forming a base on which the inner coating or lining can be formed. This patent also suffers from the deficiencies aforementioned since the solution must be cured by heating.

Although U.S. Pat. No. 3,618,613 does disclose curing by air drying, the patent still requires the use of an inner tubing to provide a base on which the outer coating can be formed. This results in force fitting of the spring over the inner tubing, which suffers from the disadvantages of providing undue forces on the spring and which also greatly increases the wall thickness, thereby lessening the kink resistance properties.

With respect to known hemostasis valves, U.S. Pat. No. 4,000,739 provides a pair of juxtaposed flexible gaskets mounted in the posterior end of the main body of the introducer sheath. The exteriorly positioned gasket of the pair is provided with a central opening which forms a seal around the catheter inserted therethrough, and the second interiorly positioned gasket is provided with a "Y" slit, the center of which is aligned with the axis of the central opening of the first gasket. The second gasket is compressed against the first gasket to seal the passage when the catheter is removed. A problem with such "Y" slit arrangement is that the slit extends through the second gasket generally in line with the longitudinal axis of the introducer sheath. As a result, when the catheter is inserted therethrough, back pressure from fluid within the introducer sheath may leak out through the slit; that is, the gaskets often do not form a complete seal against blood loss. See also U.S. Pat. No. 4,430,081. Other patents which are less relevant are U.S. Pat. Nos. 584,091; 3,620,500; 4,342,315; 4,405,316; 4,405,320; and 4,468,224.

U.S. Pat. No. 4,436,519 discloses an arrangement in which a single slit at the apex of a hemispherical projection of a gasket is provided through which the catheter is inserted. Because of the hemispherical outer surface of the projection, fluid back pressure tends to close the slit around the catheter and provide a fluid-tight seal. However, such construction is relatively complicated and also requires the use of reinforcing ribs about the hemispherical projection which further complicates the construction.

OBJECTS AND SUMMARY OF THE INVENTION

Accordingly it is an object of the present invention to provide an introducer sheath having a flexible tube for intravenous use which is kink resistant and crush resistant, without increasing the resistance to bending.

It is another object of the present invention to provide an introducer sheath having a flexible tube which has a resistance to linear compression.

It is still another object of the present invention to provide an introducer sheath having a flexible tube formed with a helical coiled spring surrounded by a protective coating, with the number of reinforcing coils per inch of tubing length being as high as 200.

It is yet another object of the present invention to provide an introducer sheath having a flexible tube formed with a helical coiled spring and a protective coating defining a cylindrical wall completely surrounding the spring, with a wall thickness as little as 0.005 inch, regardless of the diameter of the tube.

It is a further object of the present invention to provide an introducer sheath having a flexible tube formed by dipping a helical coiled spring into a liquid coating and withdrawing and air drying the coating at room temperature to form a protective coating defining a cylindrical wall completely surrounding and defining an inner and an outer wall surface therefor.

It is a still further object of the present invention to provide an introducer sheath having a valve assembly formed of a first elastic membrane having a central aperture and a second elastic membrane in sealing contact therewith and having an angled slit therein.

In accordance with an aspect of the present invention, a flexible tube for the introduction of catheters and like devices into a vascular system, includes a helical coiled spring having a plurality of coils, each of a plurality of the coils being spaced from at least one adjacent coil; and a thin cylindrical wall completely surrounding the spring and defining an inner and a substantially smooth outer wall surface, the cylindrical wall surrounding said spring having a substantially constant thickness throughout its length; the cylindrical wall prepared from a coating composition comprising a thermoplastic polymeric material dissolved in a solvent solution, said composition having a solids content that may range from about 4% to about 18%. Suitable polymers include polyurethanes, vinyl polymers such as polyvinylchloride, and elastomeric materials such latex and silicone polymers. Solvents may be selected from the group consisting of tetrahydrofuran, dioxane, methyl ethyl ketone, dimethylformamide, cyclohexane and mixtures thereof.

The above, and other, objects, features and advantages of the present invention will become readily apparent from the following detailed description thereof which is to be read in connection with the accompanying drawings.

BRIEF DESCRIPTION OF THE DRAWINGS

FIG. 1 is a longitudinal cross-sectional view of an introducer sheath according to one embodiment of the present invention;

FIG. 2 is an enlarged cross-sectional view of a portion of the flexible tube of the introducer sheath of FIG. 1;

FIG. 3 is a plan view of the interior surface of the first elastic membrane of the valve assembly shown in FIG. 1;

FIG. 4 is a plan view of the exterior surface of the second elastic membrane of the valve assembly shown in FIG. 1;

DETAILED DESCRIPTION OF THE PREFERRED EMBODIMENTS

Figure 5:
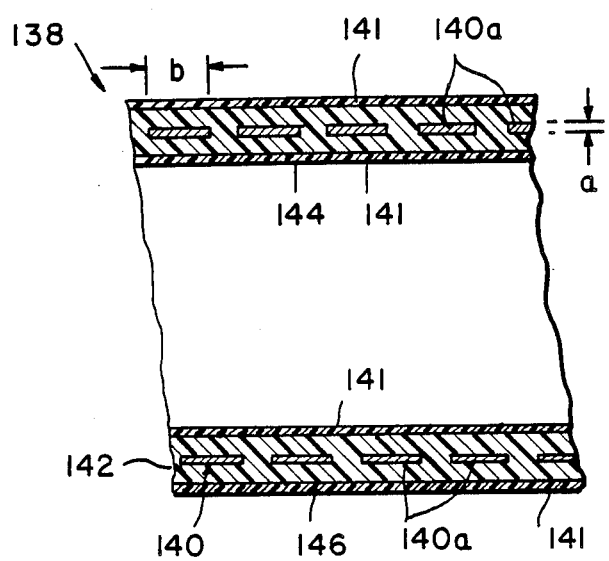
FIG. 5 is an enlarged cross-sectioned view of a portion of a first modified flexible tube that can be used with the introducer sheath of FIG. 1.

Referring to the drawings in detail, and initially to FIG. 1, an introducer sheath assembly or hemostasis cannular assembly 10 generally includes a cylindrical hub or main body portion 12 and a gradually tapered portion 14. Cylindrical hub portion 12 is open at its free end 16 and is formed with a frusto-conical configured central aperture 18 which diverges from free end 16 and extends partly through tapered portion 14. The latter tapered portion 14 is formed with a longitudinal aperture 20 of constant diameter, in fluid communication with aperture 18 and which extends to the open, free end 22 of tapered portion 14 at the outlet side of introducer sheath assembly 10. As will be appreciated from the discussion hereinafter, the diameter of longitudinal aperture 20 is slightly greater than that at the smaller diameter end of frusto-conical configured aperture 18 so as to define a circumferential shoulder 24 directed toward the outlet side of introducer sheath assembly 10.

The free end of cylindrical hub portion 12 is cut away, as at 26 to define a circumferential shoulder 28 directed toward the inlet side of introducer sheath assembly 10, and so as to also form a circumferential flange 30, as shown in FIG. 1.

In addition, an extension 32 is formed at an angle on cylindrical hub portion 12 and defines a secondary inlet port 34 formed by an aperture therein. A smaller diameter aperture 36 formed in cylindrical hub portion 12 provides fluid communication between secondary inlet port 34 and the chamber defined by frusto-conical configured aperture 18. A tube 33 is positioned within inlet port 34 for introduction of fluids therein.

In accordance with an aspect of the present invention, a flexible tube 38 for the introduction of catheters and like devices into a vascular system, is provided with a helical coiled spring 40 completely surrounded by a protective coating that defines cylindrical wall 42, as shown more clearly in FIG. 2. Although not shown, the free end of flexible tube 38 can be attached to a conventional introducing tube (not shown), but perferably, flexible tube 38 extends to a sufficent length so that such introducing tube is unnecessary.

In particular, helical coiled spring 40 includes a plurality of coils, each being spaced from an adjacent coil, although it is possible that some of the coils are tightly wound in contact with each other such that only each of a plurality of the coils is spaced from at least one adjacent coil. Although coil spacing may vary, a preferred spacing of the coils may be about 0.008 inch. Helical coiled spring 40 may be constructed of any suitable material, such as stainless steel, or even a plastic material, each coil having a diameter as low as 0.002 inch.

Because of the fineness of the coils that can be used, an extrusion coating method cannot be used for forming cylindrical wall 42 about helical coiled spring 40. Also, for this same reason and because the coils could be constructed of a plastic material, a heat treatment for forming the protective coating thereover cannot be used.

It is important in forming the protective coating that defines cylindrical wall 42, that the wall thickness thereof be relatively reduced, for example as low as 0.005 inch, while retaining the structural integrity of kink resistance, crush resistance and linear compression resistance and, at the same time, providing sufficient flexibility of tube 38. Accordingly, cylindrical wall 42 is formed from a protective coating composition comprising a thermoplastic polymeric material dissolved in a solvent solution. Generally, the composition possesses a solids content ranging from about 4% to about 18%, with a 16% solids content preferred. The thermoplastic polymeric material may be prepared from solvent-soluble materials, such as those materials selected from the group consisting of cellulose and cellulose derivatives, polyesters, polyamides, polyurethanes, vinyl polymers such as polyvinylchloride, and elastomeric materials such as latex and silicone polymers. The hardness of the polymeric material may vary, with hardness as expressed in Shore A Durometer ratings capable of ranging from about 35 to about 95. Naturally, materials possessing lower Durometer ratings are softer and will exhibit greater flexibility.

For example, a polyurethane polymer sold under the U.S. Registered Trademark "PELLETHANE CPR" No. 2103-85AE by the CPR Division of the Upjohn Company can be used as the thermoplastic polymeric material. This material has a hardness rating of approximately 87±4 measured by the Shore A Durometer Test (ASTM D 2240 Test Method).

Suitable solvents are selected from the group consisting of tetrahydrofuran, dioxane, methyl ethyl ketone, dimethylformamide, and cyclohexane, and mixtures thereof. Preferably, the solvent solution comprises a mixture of dioxane and tetrahydrofuran in a relative ratio ranging from 1:9 to 6:4, and preferably a ratio of 1:1.

Flexible tube 38 is formed by first forming the helical coiled spring 40 such that the coils thereof are spaced from each other, as previously discussed. The helical coiled spring 40 is then dipped into the aforementioned liquid coating composition, and spring 40 is then withdrawn from the composition at a rate ranging from one foot per minute to eight feet per minute, whereupon the coating is dried at room temperature to form cylindrical wall 42 that completely encloses spring 40. Drying of the coating takes approximately 15 to 30 minutes. Preferably the steps of dipping spring 40 and drying at room temperature are repeated three or four times.

Although spring 40 may remain in the solution a few seconds, it is the rate at which spring 40 is withdrawn from the solution rather than its residence time that is important. This is because a faster rate of withdrawal of spring 40 from the solution assists in retaining a greater amount of solution on spring 40. This faster withdrawal appears to counteract the forces of capillary action that tends to draw the deposited solution away from spring 40 and back into the vessel into which spring 40 was initially dipped. It has been found that a rate of between one foot per minute to eight feet per minute is a satisfactory withdrawal rate, and preferably a rate of four feet per minute is used.

As shown in FIG. 2, cylindrical wall 42 is thereby formed with a first wall thickness D surrounding each coil and a second, smaller wall thickness d at positions between adjacent spaced coils of spring 40. Accordingly, cylindrical wall 42 effectively defines an inner wall surface 44 and an outer wall surface 46, with both inner surface 44 and outer surface 46 being indented at positions between adjacent spaced coils of spring 40. As a result, the smaller wall thickness acts a hinge and thereby permits tube 38 to be highly flexible. At the same time, relatively small diameter coils can be used, and the wall thickness of flexible tube 38 can be made relatively small. This is distinguishable, for example, from U.S. Pat. No. 3,618,613 which requires the use of an inner tubing about which the spring is friction or interference fit, and whereby a larger wall thickness is provided, with less flexibility.

Preferably, tube 38 and more particularly protective coating 42, is further coated with an interpolymer 41 that preferably consists of polyvinylpyrrolidone and polyurethane. This coating 41 is hydrophilic and reduces the coefficient of friction significantly, which is important when the catheter is being introduced through the introducer sheath. The coating is also thromboresistant which is important for products of this type that are to be left in the human body for relatively long periods of time. In this regard, other thromboresistant coatings that can be used are described in U.S. Pat. Nos. 3,746,683; 3,759,788; and 4,378,803.

Alternately, interpolymer 41 may be a particular polytetrafluoroethylene polymer known commercially by the registered Trademark "TEFLON ®", manufactured by E. I. Dupont de Nemours & Co., Wilmington, Del. Specifically, particles of TEFLON ® having an average particle size of 2-3 microns may be applied to the outer surface of cylindrical wall 42 to provide outer surface lubricity. The particles may be applied to a thickness of up to about 10 microns, by spraying against the outer surface of wall 42 while it is still "wet" after its formation. Preferably, the tubes may be sprayed as the coated springs are being withdrawn from the liquid coating composition as set forth above. This alternate composition is only to be applied to the outer surface of the tubing, as TEFLON ® lacks anticoagulating properties and such properties are necessary for the inner surface of the tubing when it is to be used for blood or plasma transport.

In accordance with another aspect of the present invention, a valve assembly 48 is provided at the inlet end of introducer sheath assembly 10 and is formed of a first elastic membrane 50 and a second elastic membrane 52 in sealing contact therewith. In particular, first elastic membrane 50 has a circular configuration and is formed with an exterior surface 54 and an interior surface 56, with a circumferential flange 58 extending from interior surface 56 and spaced inwardly from the outer circular edge 60 of membrane 50. As shown in FIGS. 1 and 3, first elastic membrane 50 is formed with a central aperture 62 which converges from exterior surface 54 toward interior surface 56. The diameter of central aperture 62 at the interior surface 56 is as small as 0.032 inches which will seal around the guide wire that is introduced into an artery.

Second elastic membrane 52 is formed in a circular configuration and includes an exterior surface 64 and an interior surface 66 with a slit 68 extending between exterior surface 64 and interior surface 64 and interior surface 66. Slit 68 passes through the center 70 of exterior surface 64 and is angled toward interior surface 66, as shown in FIGS. 1 and 4. Because of such angle, when a catheter is withdrawn, the back pressure of fluid within the chamber defined by frusto-conical configured aperture 18 provides a positive closure and sealing arrangement to prevent the escape of fluid.

In constructing and mounting valve assembly 48, the outer diameter of second elastic membrane 52 is substantially equal to the inner diameter of flange 58 such that second elastic membrane 52 fits within flange 58 to provide a sealing contact therewith. At the same time, the exterior surface 64 of second elastic membrane 52 is positioned in sealing contact with the interior surface 56 of first elastic membrane 50. In such position, it will be appreciated that center 70 of exterior surface 64, through which slit 68 passes, is in axial alignment with the central axis of aperture 62 of first elastic membrane 50.

In this regard, the present invention provides a relatively simple, yet novel, construction of a valve assembly, which provides positive prevention of fluid, that is, prevents fluid loss.

In operation of the valve assembly, first elastic membrane 50 having central aperture 62 will maintain a sealing relationship with a catheter introduced into an artery. Upon withdrawal of the catheter from the passage, second elastic membrane 52 having slit 68 will provide a sealing arrangement with the catheter, thus preventing blood leakage.

Referring now to FIG. 5, there is shown a flexible tube 138 which can be used in place of flexible tube 38 of FIG. 1, in which like elements are represented by the same numerals augmented by 100, and a detailed description of such like elements will be omitted herein for the sake of brevity.

In particular, flexible tube 138 for the introduction of catheters and like devices into a vascular system, is provided with a helical coiled spring 140 completely surrounded by a protective coating that defines a cylindrical wall 142. Helical coiled spring 140 includes a plurality of coils 140a, each being spaced from an adjacent coil, although it is possible that some of the coils are tightly wound in contact with each other so that only each of a plurality of the coils are spaced from at least one adjacent coil. While the exact spacing of coils 140a may vary, coil spacing may range to approximately 0.008 inch. This spacing achieves a desirable uniformity in the thickness of cylindrical wall 142.

The coils 140a of helical coiled spring 140 are constructed in a rectangular configuration in cross-section, with a second dimension "a" of each coil 140a in the radial direction of flexible tube 138 being smaller than a first dimension "b" thereof in the lengthwise direction of flexible tube 138. Thus, the first dimension of helical coiled spring 140 may be up to about ten times larger than the second dimension. For example, the dimension "a" can be 0.002 inch, while the dimension "b" can be 0.020 inch. The dimension "b" should preferably be within the range of 0.010 inch to 0.2 inch. However, it is only necessary that the dimension "b" be greater than the dimension "a" to provide excellent flexibility characteristics for flexible tube 138. Helical coiled spring 140 may be constructed of any suitable materials, such as stainless steel or even a plastic material.

Cylindrical wall 142 is formed from a protective coating composition which is identical to that disclosed with the emobodiment of FIGS. 1-4, and is formed on and in surrounding relation to helical coiled spring 140 in the same manner.

However, unlike the embodiment of FIGS. 1-4, cylindrical wall 142 is formed with substantially flat, smooth inner and outer wall surfaces 144 and 146, whereby cylindrical wall 142 has a substantially constant thickness throughout its entire length. It has been found that, because of the composition of cylindrical wall 142 and the use of helical coiled spring 140, excellent flexiblity characteristics, are obtained, whereby the space between adjacent coils 140a acts like flexible links in a chain, even with the substantially constant wall thickness.

Further, an interpolymer 141 is formed over inner and outer wall surfaces 144 and 146 as in the embodiment of FIGS. 1-4.

With the arrangement of FIG. 5, distinct advantages are provided over the embodiment of FIG. 2 by the provision of the smooth outer wall surface 146, which provides more comfort to the patient when inserted through the skin.

Figure 6:
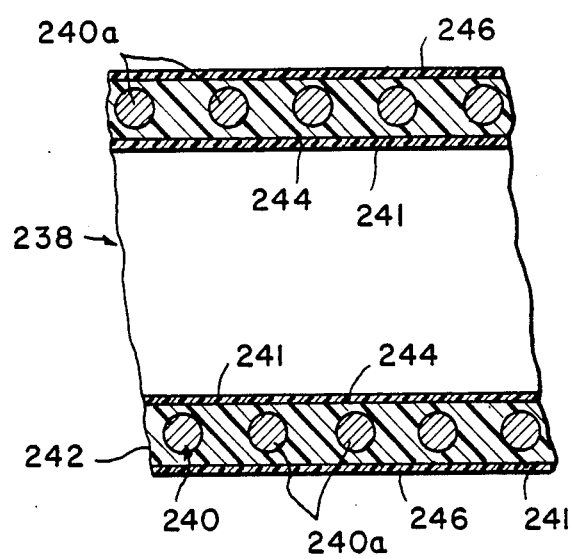
FIG. 6 is an enlarged cross-sectional view of a portion of a second modified flexible tube that can be used with the introducer sheath of FIG. 1.

Referring now to FIG. 6, there is shown a further modification of the embodiment of FIG. 5, with like elements being represented by the same numerals augmented by a further 100, and a detailed description of such like elements will be omitted herein for the sake of brevity. Specifically, in the embodiment of FIG. 6, each coil 240a of helical coiled spring 240 has a circular shape in cross-section, as in the embodiment of FIG. 2. However, outer wall surface 246 is still formed as a flat, smooth surface, with cylindrical wall 242 having a substantially constant thickness throughout its entire length.

Figure 7:
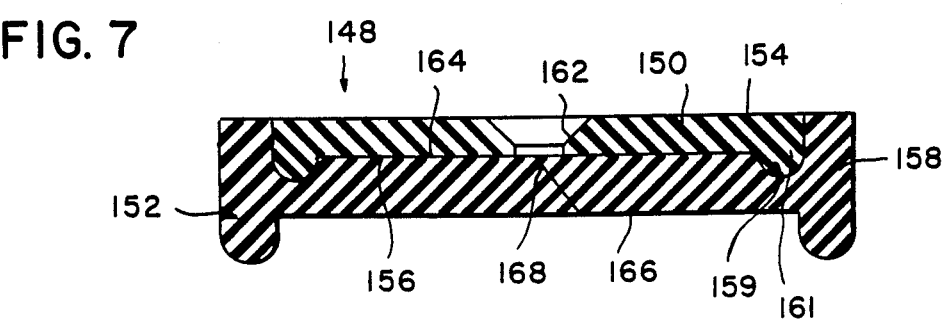
FIG. 7 is an enlarged cross-sectional view of a modified valve assembly according to the present invention.

Referring now to FIG. 7, there is shown a modified arrangement of a valve assembly 148 according to the present invention in which elements similar to those of valve assembly 48 are represented by the same numerals augmented by 100, and a detailed description thereof will be omitted herein for the sake of brevity. Specifically, in the embodiment of FIG. 1, membrane 52 fits within membrane 50. The reverse is true in the embodiment of FIG. 7 in which membrane 150 fits within membrane 152. Thus, membrane 152 is formed with an outer, annular flange 158 which fits within the cut away portion 26. Flange 158, as shown in FIG. 7 extends to a height above and below the main disk section of elastic membrane 152. Thus, exterior surface 164 is surrounded by an annular wall defined by flange 158. In addition, an annular recessed ring 159 is formed in exterior surface 164 adjacent to flange 158 and an annular peripheral bead 161 extends from interior surface 156 of membrane 150 and fits within recessed ring 159 in sealing relation.

Having described specific preferred embodiments of the present invention with reference to the accompanying drawings, it is to be understood that the present invention is not limited to those precise embodiments, and that various changes and modifications may be effected therein by one of ordinary skill in the art without departing from the spirit or scope of the present invention as defined by the appended claims.

I claim:

1. A flexible tube for the introduction of catheters and like devices into a vascular system, comprising:
    a helical coiled spring having a plurality of coils, each of a plurality of said coils being spaced from at least one adjacent coil; and
    a thin cylindrical wall prepared from a protective coating composition completely surrounding said spring to define an inner wall surface and a substantially smooth outer wall surface, said cylindrical wall surrounding said spring having a substantially constant thickness throughout its length;
    said coating composition comprising a thermoplastic polymeric material dissolved in a solvent solution, said composition having a solids content ranging from about 4% to about 18%, and said solution comprising a solvent selected from the group consisting of tetrahydrofuran, dioxane, methyl ethyl ketone, dimethylformamide, cyclohexane, and mixtures thereof.

2. A flexible tube according to claim 1; wherein said solvent solution comprises a mixture of dioxane and tetrahydrofuran in a relative ratio ranging from 1:9 to 6:4 by weight.

3. A flexible tube according to claim 2; wherein said relative ratio is 1:1.

4. A flexible tube according to claim 1; wherein said polymeric material is selected from the group consisting of cellulose, cellulose derivatives, polyesters, polyamides, polyurethane, polyvinyl chloride, latex and silicone.

5. A flexible tube according to claim 1; wherein said composition has a solids content of 16%.

6. A flexible tube according to claim 1; wherein said polymeric material is a solid material having a Shore A hardness rating ranging from about 35 to about 95.

7. A flexible tube according to claim 1; wherein the first thickness of said cylinder is at least as small as 0.005 inch.

8. A flexible tube according to claim 1; wherein said cylindrical wall further includes a lubricating coating on at least one of its surfaces.

9. A flexible tube according to claim 8; wherein said lubricating coating is selected from the group consisting of a polyvinylpyrrolidone-polyurethane interpolymer and polytetrafluoroethylene.

10. A flexible tube according to claim 9; wherein said lubricating coating comprises polytetrafluoroethylene.

11. A flexible tube according to claim 10; wherein said polytetrafluoroethylene comprises particles having an average particle size of 2-3 microns.

12. A flexible tube according to claim 10; wherein said polytetrafluoroethylene is applied to a thickness of up to about 10 microns.

13. A flexible tube according to claim 10; wherein said polytetrafluoroethylene is applied to said cylindrical wall while the coating material comprising the said wall is wet.

14. A flexible tube according to claim 8; wherein said lubricating coating is also a thrombroresistant coating.

15. A flexible tube according to claim 14; wherein said thromboresistant coating is a polyvinylpyrrolidone-polyurethane interpolymer.

16. A flexible tube according to claim 1; wherein each coil of said coiled spring has a rectangular shape in cross-section.

17. A flexible tube according to claim 16; wherein said rectangular shape of each coil has a first dimension in the lengthwise direction of said tube and a second dimension in the radial direction of said tube which is smaller than said first dimension.

18. A flexible tube according to claim 17; wherein said first dimension is up to about ten times larger than said second dimension.

19. A flexible tube according to claim 1; wherein each coil of said coiled spring has a circular shape in cross-section.

20. An introducer sheath comprising:
connector means having opposite ends, one of said ends defining a first inlet and the other end defining an outlet, an opening extending end to end therethrough to fluidly connect said first inlet and said outlet, and a second inlet in fluid communication with said opening;
a flexible tube fluidly connected to said outlet, said flexible tube including a helical coiled spring having a plurality of coils, each of a plurality of said coils being spaced from at least one adjacent coil, and a thin cylindrical wall prepared from a protective coating composition completely surrounding said spring to define an inner wall surface and a substantially smooth outer wall surface, said cylindrical wall surrounding said spring having a substantially constant thickness throughout its length, said coating composition comprising a thermoplastic polymeric material dissolved in a solvent solution, said composition having a solids content ranging from about 4% to about 18%, and said solution comprising a solvent selected from the group consisting of tetrahydrofuran, dioxane, methyl ethyl ketone, dimethylformamide, cyclohexane and mixtures thereof; and
a valve assembly mounted at said first inlet, said valve assembly including a first elastic membrane having a first exterior surface, a first interior surface and an aperture extending between said first exterior and interior surfaces, and a second elastic membrane having a second exterior surface in sealing contact with said first interior surface of said first elastic membrane, a second interior surface, and a slit extending between said second exterior and interior surfaces at an angle from the direction of fluid flow in said introducer sheath, said slit being in fluid communication with said opening and said aperture.

21. An introducer sheath according to claim 20; wherein said solvent solution includes dioxane and tetrahydrofuran in a relative ratio ranging from 1:9 to 6:4 by weight.

22. An introducer sheath according to claim 21; wherein said relative ratio is 1:1.

23. An introducer sheath according to claim 20; wherein said polymeric material is selected from the group consisting of cellulose, cellulose derivatives, polyesters, polyamides, polyurethane, polyvinyl chloride, latex and silicone.

24. An introducer sheath according to claim 20; wherein said aperture converges from said first exterior surface toward said first interior surface and is centrally positioned within said first elastic membrane.

25. A flexible tube according to claim 20; wherein each coil of said coiled spring has a rectangular shape in cross-section.

26. A flexible tube according to claim 25; wherein said rectangular shape of each coil has a first dimension in the lengthwise direction of said tube and a second dimension in the radial direction of said tube which is smaller than said first dimension.

27. A flexible tube according to claim 26; wherein said first dimension is approximately ten times larger than said second dimension.

28. A flexible tube according to claim 20; wherein each coil of said coiled spring has a circular shape in cross-section.

* * * * *